(12) United States Patent
Borody et al.

(10) Patent No.: US 7,993,682 B2
(45) Date of Patent: Aug. 9, 2011

(54) ELECTROLYTE PURGATIVE

(76) Inventors: Thomas Julius Borody, Five Dock (AU); Sanjay Ramrakha, Five Dock (AU); John Saxon, Five Dock (AU); Antony Wettstein, Five Dock (AU)

( * ) Notice: Subject to any disclaimer, the term of this patent is extended or adjusted under 35 U.S.C. 154(b) by 1000 days.

(21) Appl. No.: 10/506,728

(22) PCT Filed: Mar. 4, 2003

(86) PCT No.: PCT/AU03/00257
§ 371 (c)(1),
(2), (4) Date: Jun. 27, 2005

(87) PCT Pub. No.: WO03/074061
PCT Pub. Date: Sep. 12, 2003

(65) Prior Publication Data
US 2005/0271749 A1    Dec. 8, 2005

(30) Foreign Application Priority Data
Mar. 4, 2002    (AU) ..................... PS08871

(51) Int. Cl.
*A61K 33/14*    (2006.01)
*A61K 31/715*    (2006.01)
*A61K 31/4402*    (2006.01)

(52) U.S. Cl. ........ 424/722; 424/679; 424/697; 424/680; 514/54

(58) Field of Classification Search .................. 424/722, 424/78.01, 679, 697, 680; 514/54, 892
See application file for complete search history.

(56) References Cited

U.S. PATENT DOCUMENTS

| | | | | |
|---|---|---|---|---|
| 4,186,025 A | * | 1/1980 | Kang et al. ............... | 106/125.1 |
| 4,452,779 A | * | 6/1984 | Cockerill ................ | 424/601 |
| 4,766,004 A | * | 8/1988 | Moskowitz ............... | 426/658 |
| 4,975,286 A | * | 12/1990 | Hechter .................. | 424/682 |
| 5,173,296 A | * | 12/1992 | Andre et al. ............. | 424/738 |
| 5,196,205 A | | 3/1993 | Borody .................. | 424/653 |
| 5,232,699 A | * | 8/1993 | Colliopoulos ............. | 424/738 |
| 5,274,001 A | | 12/1993 | Borody .................. | 514/474 |
| 5,443,826 A | | 8/1995 | Borody .................. | 424/93.3 |
| 5,476,669 A | | 12/1995 | Borody .................. | 424/653 |
| 5,519,014 A | | 5/1996 | Borody .................. | 514/159 |
| 5,858,403 A | | 1/1999 | Borody et al. ........... | 424/456 |
| 6,103,268 A | | 8/2000 | Borody et al. ........... | 424/489 |
| 6,121,250 A | | 9/2000 | Nishiyama et al. ......... | 514/57 |
| 6,132,767 A | | 10/2000 | Borody et al. ........... | 424/456 |
| 6,162,464 A | * | 12/2000 | Jacob et al. ............. | 424/456 |
| 6,277,836 B1 | | 8/2001 | Borody .................. | 514/159 |
| 6,426,338 B1 | | 7/2002 | Borody .................. | 514/159 |
| 6,475,518 B1 | | 11/2002 | Baumgart ................ | 424/451 |
| 6,489,317 B1 | | 12/2002 | Borody .................. | 514/197 |
| 6,551,632 B2 | | 4/2003 | Borody .................. | 424/780 |
| 6,645,530 B1 | | 11/2003 | Borody .................. | 424/543 |
| 6,774,111 B1 | | 8/2004 | Wolf et al. .............. | 514/23 |
| 2002/0035075 A1 | | 3/2002 | Borody .................. | 514/28 |
| 2003/0180260 A1 | | 9/2003 | Clancy et al. ............ | 424/934 |
| 2004/0009961 A1 | | 1/2004 | Borody .................. | 514/171 |
| 2004/0028689 A1 | | 2/2004 | Borody .................. | 424/184.1 |
| 2004/0038329 A1 | | 2/2004 | Clancy et al. ............ | 435/30 |

FOREIGN PATENT DOCUMENTS

| | | |
|---|---|---|
| CA | 2335713 A1 * | 1/2001 |
| EP | 0397689 | 11/1990 |
| EP | 0433299 | 6/1991 |
| EP | 0439453 | 8/1991 |
| EP | 0554291 | 8/1993 |
| EP | 0771562 | 5/1997 |
| JP | 05306221 | 11/1993 |
| RU | 2098100 | 12/1997 |
| WO | WO8501441 | 4/1985 |
| WO | WO8605981 | 10/1986 |
| WO | WO8903219 | 4/1989 |
| WO | WO8905659 | 6/1989 |
| WO | WO9001335 | 2/1990 |
| WO | WO9206690 | 4/1992 |
| WO | WO9602236 | 2/1996 |
| WO | WO9611014 | 4/1996 |
| WO | WO9843667 | 10/1998 |
| WO | WO9850043 | 11/1998 |
| WO | WO9956749 | 11/1999 |
| WO | WO0001378 | 1/2000 |

(Continued)

OTHER PUBLICATIONS

Schiller, L.R., Review article: The Therapy of Constipation, 2001, Alimentary Pharmacology and Theraputics, vol. 15, pp. 749-763.*

(Continued)

*Primary Examiner* — Johann Richter
*Assistant Examiner* — Andriae M Holt
(74) *Attorney, Agent, or Firm* — Gavrilovich, Dodd & Lindsey; Gregory P Einhorn

(57) ABSTRACT

The invention relates to compositions for use in purgatives, to purgatives comprising such compositions, and to methods for inducing purgation of the colon. The composition may comprise at least one water-soluble sodium salt; at least one water-soluble minimally degradable sugar in an amount, by weight, of from about 1 to about 3 times the weight of sodium ions in said composition; at least one water-soluble potassium salt in an amount, by weight, of from about 0.05 to about 1 time the weight of said sodium salt in said composition; and at least one water-soluble magnesium salt, wherein the weight of magnesium ions in said composition is from 0.1 to about 10 times the weight of sodium ions in said composition.

15 Claims, No Drawings

FOREIGN PATENT DOCUMENTS

| WO | WO 01/67895 | * | 9/2001 |
|---|---|---|---|
| WO | WO0180852 | | 11/2001 |
| WO | WO0197821 | | 12/2001 |
| WO | WO0203065 | | 1/2002 |
| WO | WO0207741 | | 1/2002 |
| WO | WO03061767 | | 7/2003 |
| WO | WO2004070043 | | 8/2004 |

OTHER PUBLICATIONS

JP 07242539 A, Fukahori et al., Compositions having laxative effect, used in treatment of constipation comprise organic acid, sugar alcohol, and optional calcium salts, 1995, Derwent Abstract, pp. 1-7.*

Dye, D., "The inadequacy of the usual determinative tests for the identification of Xanthomonas SPP," New Zealand Journal of Science 5(4):393-416 (1962).

Altomare DF, Memeo V, "Colonic explosion during diathermy colotomy. Report of a case", *Diseases Colon Rectum Mar*;36(3):291-2 (1993).

Andrews PJ, Borody TJ, "'Putting back the bugs': bacterial treatment relieves chronic constipation and symptoms of irritable bowel syndrome ", *Med J Aust. Nov. 1*;159(9):633-4 (1993).

Arieff AI, Llach F, Massry SG, "Neurological manifestations and morbidity of hyponatremia: correlation with brain water and electrolytes", *Medicine (Baltimore) Mar*;55(2):121-9 (1976).

Borody TJ, "'Flora Power'—fecal bacteria cure chronic C. difficile diarrhea", *Am J Gastroenterol. Nov*;95(I I):3028-9 (2000).

Borody TJ, "Helicobacter pylori eradication failure—'salvage' therapies needed", *Ital J Gastroenterol Hepatol. Aug*;30(4):375-7 (1998).

Borody TJ, Andrews P, Jankiewicz E, Ferch N, Carroll M, "Apparent reversal of early gastric mucosal atrophy after triple therapy for Helicobacter pylori", *Am J Gastroenterol. Aug*;88(8):1266-68 (1993).

Borody TJ, Ashman O., "Lactoferrin: milking ulcers?", *Dig Liver Dis. Oct*.;35(10):691-3. (2003).

Borody TJ, Brandl S, Andrews P, Ferch N, Jankiewicz E, Hyland L, "Use of high efficacy, lower dose triple therapy to reduce side effects of eradicating Helicobacter pylori", *Am J Gastroenterol. Jan*;89(1):33-8 (1994).

Borody TJ, George L, Andrews P, Brandl S, Noonan S, Cole P, Hyland L, Morgan A, Maysey J, Moore-Jones D, "Bowel-flora alteration: a potential cure for inflammatory bowel disease and irritable bowel syndrome?", *Med J Aust. May 15*;150(10):604 (1989).

Borody TJ, George LL, Brandt S, Andrews P, Lenne J, Moore-Jones D, Devine M, Walton M, "Helicobacter pylori eradication with doxycycline-metronidazole-bismuth subcitrate triple therapy", *Scand J Gastroenterol. Apr*.;27(4):281-4 (1992).

Borody TJ, Shortis NP, Reyes E, "Eradication therapies for Helicobacter pylori", *J Gastroenterol. 33 Suppl* 10:53-6 (1998).

Borody TJ, Warren EF, Leis S, Surace R, Ashman O, "Treatment of ulcerative colitis using fecal bacteriotherapy", *J Clin Gastroenterol. Jul*;37(1):42-7 (2003).

Borody TJ, Warren EF, Leis SM, Surace R, Ashman O, Siarakas S., "Bacteriotherapy using fecal flora: toying with human motions", *J Clin Gastroenterol Jul*;38(6):475-83 (2004).

Cohen CD, Keuneke C, Schiemann U, Schroppel B, Siegert S, Rascher W, Gross M, Schlondorff D, "Hyponatraemia as a complication of colonoscopy", *Lancet Jan 27*;357(9252):282-3 (2001).

de Boer WA, Borody TJ, "Treatment failures and secondary resistance to antibiotics. A growing concern in Helicobacter pylori therapy", *Dig Liver Dis. Nov*;32(8):673-5 (2000).

Derwent Abstract Accession No. 93-408836, Class B05, JP 05306221 A (Horii Yakunhin Kogyo KK) Nov. 19, 1993 Abstract Only.

Derwent Abstract Accession No. 98-375395, Class B05, RU 2098100 C1 (Maksimova et al.) Dec. 10, 1997 Abstract Only.

Fincher RK, Osgard EM, Jackson JL, Strong JS, Wong RK, "A comparison of bowel preparations for flexible sigmoidoscopy: oral magnesium citrate combined with oral bisacodyl, one hypertonic phosphate enema, or two hypertonic phosphate enemas", *Am J Gastroenterol Aug*.;94(8):2122-7 (1999).

Fraser CL, Kucharczyk J, Arieff AI, Rollin C, Sarnacki P, Norman D, "Sex differences result in increased morbidity from hyponatremia in female rats", *Am J Physiol. Apr*;256(4 Pt 2):R880-5 (1989).

Melton JE, Patlak CS, Pettigrew KD, Cserr HF "Volume regulatory loss of Na, C1, and K from rat brain during acute hyponatremia", *Am J Physiol. Apr*;252(4 Pt 2):F661-9 (1987).

Certified English language translation of Japanese Patent Document No. JP 05306221, Kawakami, Y., "Intestinal canal irrigation solution composition and intestinal canal irrigation solution," Nov. 19, 1993.

* cited by examiner

ELECTROLYTE PURGATIVE

This application is the National Stage of International Application. No. PCT/AU03/00257, filed 4 Mar. 2003, and claims benefit of priority under 35 U.S.C. §365(b) to Australia Provisional Application No. PS 08871, filed 4 Mar. 2002. The subject matter of each of the above-noted applications is incorporated herein by reference in its entirety.

FIELD OF THE INVENTION

The invention relates to compositions for use in purgatives, to purgatives comprising such compositions, and to methods for inducing purgation of the colon.

BACKGROUND ART

Colonic orthostatic lavage is an iatrogenic phenomenon related to the administration of a purgative and therefore is predictable in its action and side effects. It is important to make the distinction between the use of iatrogenic purgation solutions and fluid/electrolyte replacement solutions used for treatment of vomiting and diarrhoea associated with gastroenteritis. The use of mainly hypotonic or isotonic solutions such as glucose-based 'Bangladesh' solution and rice-based solutions has been successful in patients with gastroenteritis and dehydration, a highly unpredictable disease. The physiological principle of coupled sodium and glucose transport in a 1:1 molar ratio in the intestine has been shown to be safe and effective.

Purgatives developed to date for orthostatic lavage to clean the bowel of faecal matter prior to colonoscopy have taken the form of either and isotonic, large volume lavage (e.g. Braintree's Golytely) or more hypertonic lavage products such as Fleet's sodium phosphate or sodium picosulfate (Picolax) products. The former generally cause little homeostatic disturbance or intra-vascular sodium and other electrolytes or fluid shifts because of their isotonic nature, which minimizes electrolyte absorption/secretion by the presence of high molecular weight polyethylene glycol (PEG mw 3350). However, these preparations have recently been reported to be associated with hyponatremia (Cohen D.C., et al., *Lancet* 357(9252): 282-283 (2001)). Products with sodium phosphate and sodium picosulfate are felt to be better tolerated (Fincher RK, et al., *Am. J. Gastroenterol.* 94(8): 2122-7 (1999)). However, these products have also been associated with a significant hypo-osmolar state and electrolyte imbalance, particularly hyponatremia. This, to a large extent, is contributed to by a loss of electrolytes through the resultant diarrhea caused by the lavage with concomitant replacement of this loss by water (without electrolytes) leading to hyponatremia and water intoxication associated with a hypo-osmolar state.

The symptoms of headache, lethargy and nausea reported by patients undergoing orthostatic lavage are felt to be due to an osmotic shift with resultant dilutional hyponatremia that is induced by the various bowel preparation products such as "Fleet", Picolax etc. This effect appears to be more pronounced in adult females, perhaps as a result of relatively less total body water when compared to adult males and children (Fraser et al., *Am. J. Physiol.* 256: R880-5 (1989)).

The clinical features of hyponatremia (hypoosmolality) are highly variable and their severity correlates poorly with the level of serum sodium. Classically, the clinical features of severe hyponatremia are confusion, seizures and obtundation.

A decrease in plasma osmolality causes brain swelling (cerebral oedema) as water moves along osmotic gradients. In response, the brain loses solute from the intra- and extracellular fluid spaces, which returns brain water content back towards normal. Once the brain has equilibrated (i.e. volume-adapted) through solute losses, neurological features will be less prominent or resolve.

The rate of fall of serum osmolality is generally better correlated with morbidity and mortality than the actual magnitude of the decrease (Arieff, A. I. et al., *Medicine (Baltimore)* 55: 121-9 (1976)), and is somewhat arbitrarily defined as hypoosmolality developing over 24 to 48 hours. Mortality up to 50% has been reported in patients with acute hyponatremia (Arieff, A. I. et al., loc.cit.). Cerebral oedema develops when hypoosmolality exceeds the ability of the brain to regulate its volume by solute losses. In experimental models, acute hyponatremia results in the loss of sodium and chloride from the brain within 30 minutes, whilst potassium loss is more delayed. All electrolyte losses are maximal by 3 hours after initiation of hyponatremia (Melton, J. E. et al., *Am. J. Physiol.* 252: F661-9 (1987)).

Hence in some situations the effects of the various bowel purgative formulations currently available can lead to the unpleasant side effects of headache, malaise and dizziness and hypotension. Additionally, life threatening presentations of hypo-osmolar grand mal epileptic seizures, asphyxia and death have been reported.

Due to the accepted benefits of screening colonoscopic surveillance programs for the detection of colonic polyps and bowel cancer, the utilisation of colonic lavage is increasing rapidly. Indeed it is feasible that a large number of the population over the age of 50 years is likely to undergo colonoscopic examination. As a result, a considerable number of patients could potentially develop lavage-related hyponatremia and hypo-osmolar water intoxication with subsequent 'dilution' of other electrolytes leading to significant morbidity and potentially mortality.

Poor palatability leading to reduced patient compliance has been an important issue in the failure of some of the currently available products; either the volume is too large or the taste too objectionable for certain patients to comply with taking the prescribed bowel preparation. This leads to inadequate orthostatic lavage causing poor visibility at colonoscopy.

There is therefore a need for a purgative composition that reduces mortality and/or patient morbidity and/or which makes the procedure of purgation of the colon much more pleasant for the patient so as to facilitate patient compliance.

The present invention therefore provides novel electrolyte-enhanced purgatives which may be administered in relatively small liquid volumes, suitably in the form of a palatable soup mixture, but which may also be formulated in various other forms such as capsules, powders or compressed tablets. Thus, the compositions and purgatives of the present invention cause a purgative effect while ameliorating or overcoming the disadvantages associated with the administration of prior art purgatives, namely (a) symptoms associated with osmotic shifts and electrolyte imbalance; (b) hyponatremia; and (c) poor patient compliance owing to unpalatibility and/or the need to consume large volumes of liquid.

SUMMARY OF THE INVENTION

In a first embodiment, the invention provides a composition for use in a purgative, the composition comprising:
  (i) at least one water-soluble sodium salt;

(ii) at least one water-soluble minimally degradable sugar in an amount, by weight, of from about 1 to about 3 times the weight of sodium ions in said composition;

(iii) at least one water-soluble potassium salt in an amount, by weight, of from about 0.05 to about 1 times the weight of said sodium salt in said composition; and (iv) at least one water-soluble magnesium salt, wherein the weight of magnesium ions in said composition is from about 0.1 to about 10 times the weight of sodium ions in said composition.

In a second embodiment, the invention provides a purgative, comprising a hypertonic aqueous solution of the composition of the first embodiment.

In a third embodiment, the invention provides a method of inducing purgation of the colon of a patient in need thereof, comprising administering to said patient a composition of the first embodiment or a purgative of the second embodiment in an amount effective to induce purgation of the patient's colon.

In a fourth embodiment, the invention provides the use of a composition of the first embodiment for the manufacture of a purgative for inducing purgation of the colon.

In a fifth embodiment, the invention provides a method for the treatment or prevention of one or more of a member selected from the group consisting of lavage-associated hyponatremia, hypoosmolality, nausea, malaise, vomiting, headache and convulsions, comprising administering to a patient in need of such treatment a composition of the first embodiment or a purgative of the second embodiment.

In a sixth embodiment, the invention provides use of a composition of the first embodiment for the manufacture of a medicament for the treatment or prevention of one or more of a member selected from the group consisting of lavage-associated hyponatremia, hypoosmolality, nausea, malaise, vomiting, headache and convulsions.

In a seventh embodiment, the invention provides a method for the treatment or prevention of acute gastrointestinal infections, comprising administering to a patient in need of such treatment a composition of the first embodiment or a purgative of the second embodiment.

In an eighth embodiment, the invention provides use of a composition of the first embodiment for the manufacture of a medicament for the treatment or prevention of acute gastrointestinal infections.

In a ninth embodiment, the invention provides a method for the treatment or prevention of constipation, acute constipation, chronic constipation or constipation predominant irritable bowel syndrome, comprising administering to a patient in need of such treatment a composition of the first embodiment or a purgative of the second embodiment.

In a tenth embodiment, the invention provides use of a composition of the first embodiment for the manufacture of a medicament for the treatment or prevention of constipation, acute constipation, chronic constipation or constipation predominant irritable bowel syndrome.

In an eleventh embodiment, the invention provides the composition of the first embodiment or the purgative of the second embodiment when used in pre-colonoscopic or pre-surgical lavage, as a simple purgative, as electrolyte replacement lavage, as a barium enema preparation, in CT "virtual colonoscopy", in radiological applications, as electrolyte replacement lavage solutions, as electrolyte replacement lavage solutions for acute gastrointestinal infections, for symptomatic treatment in patients suffering from acute or chronic constipation or related symptoms or constipation predominant irritable bowel syndrome, as a regular laxative, or for the treatment or prevention of lavage-associated hyponatremia, hypoosmolality, nausea, malaise, vomiting, headache or convulsions.

In a twelfth embodiment, the invention provides a composition for use in a purgative, the composition comprising:

(i) at least one water-soluble sodium salt;

(ii) at least one water-soluble degradable sugar in an amount, by weight, of from about 1 to about 3 times the weight of sodium ions in said composition;

(iii) at least one water-soluble potassium salt in an amount, by weight, of from about 0.05 to about 1 times the weight of said sodium salt in said composition; and (iv) at least one water-soluble magnesium salt, wherein the weight of magnesium ions in said composition is from about 0.1 to about 10 times the weight of sodium ions in said composition.

In a thirteenth embodiment, the invention provides a purgative, comprising a hypertonic aqueous solution of the composition of the twelfth embodiment.

In a fourteenth embodiment, the invention provides a method of inducing purgation of the colon of a patient in need thereof, comprising administering to said patient in the absence of diathermy a composition of the twelfth embodiment or a purgative of the thirteenth embodiment in an amount effective to induce purgation of the patient's colon.

In a fifteenth embodiment, the invention provides the use of a composition of the twelfth embodiment for the manufacture of a purgative for inducing purgation of the colon in the absence of diathermy.

In a sixteenth embodiment, the invention provides a method for the treatment or prevention of one or more of a member selected from the group consisting of lavage-associated hyponatremia, hypoosmolality, nausea, malaise, vomiting, headache and convulsions, comprising administering to a patient in need of such treatment in the absence of diathermy a composition of the twelfth embodiment or a purgative of the thirteenth embodiment.

In a seventeenth embodiment, the invention provides use of a composition of the twelfth embodiment for the manufacture of a medicament for the treatment or prevention in the absence of diathermy of one or more of a member selected from the group consisting of lavage-associated hyponatremia, hypoosmolality, nausea, malaise, vomiting, headache and convulsions.

In an eighteenth embodiment, the invention provides a method for the treatment or prevention of acute gastrointestinal infections, comprising administering to a patient in need of such treatment in the absence of diathermy a composition of the twelfth embodiment or a purgative of the thirteenth embodiment.

In a nineteenth embodiment, the invention provides use of a composition of the twelfth embodiment for the manufacture of a medicament for the treatment or prevention of acute gastrointestinal infections in the absence of diathermy.

In a twentieth embodiment, the invention provides a method for the treatment or prevention of constipation, acute constipation, chronic constipation or constipation predominant irritable bowel syndrome, comprising administering to a patient in need of such treatment in the absence of diathermy a composition of the twelfth embodiment or a purgative of the thirteenth embodiment.

In a twenty-first embodiment, the invention provides use of a composition of the twelfth embodiment for the manufacture of a medicament for the treatment or prevention of constipation, acute constipation, chronic constipation or constipation predominant irritable bowel syndrome in the absence of diathermy.

In a twenty-second embodiment, the invention provides the composition of the twelfth embodiment or the purgative of the thirteenth embodiment when used in the absence of diathermy in pre-colonoscopic or pre-surgical lavage, as a simple purgative, as electrolyte replacement lavage, as a barium enema preparation, in CT "virtual colonoscopy", in radiological applications, as electrolyte replacement lavage solutions, as electrolyte replacement lavage solutions for acute gastrointestinal infections, for symptomatic treatment in patients suffering from acute or chronic constipation or related symptoms or constipation predominant irritable bowel syndrome, as a regular laxative, or for the treatment or prevention of lavage-associated hyponatremia, hypoosmolality, nausea, malaise, vomiting, headache or convulsions.

As used herein, unless the context clearly indicates otherwise, the words "comprise", "comprises", "comprising" or other variations thereof shall be understood as meaning that the stated integer or integers is/are included and does not exclude other integers from being present even though those other integers are not explicitly stated.

The combined effects of the water-soluble sodium, potassium and magnesium salts and the minimally degradable sugar(s) in the compositions and purgatives of the invention cause a purgative effect which is surprisingly greater than the effect that would have been expected from the known effects of the same amounts of the individual components of the compositions. That is, the amounts of the salts required for simply performing their known purgative function would be significantly greater if they were used singly. Furthermore, the other benefits of the compositions and purgatives of the present invention are not provided by compositions of only a single component. Additionally, the increased tonicity of the present purgatives compared to existing products enables a reduction in the amount of each constituent while maintaining the desired purgative effect. Thus, the components of the purgatives of the invention cooperate to provide a purgative which is palatable and which causes purgation without the side effects seen with prior art compositions, in a way that could not have been predicted prior to the present invention.

The invention provides formulations, which safely achieve orthostatic bowel lavage without associated hypo-osmolar hyponatremia. Furthermore, the inventors have found that these formulations can achieve rapid resolution and symptom reversal together with electrolyte replacement in certain infective conditions of the gastrointestinal tract. The compositions of the invention may also be used for patients with either acute or chronic constipation, since their purgative effect, secondary to combined hypertonic effect, is not associated with melanosis seen particularly in patients taking senna-containing faecal softening agents.

The additional function of the compositions is to combine sugar and sodium in amounts that assist in transluminal absorption of sodium and water. Individually, oral rehydration solutions (compositions) utilise this principle. However the compositions of the present invention have the unique and surprising feature of causing a purgative effect while performing the function of assisting in transluminal absorption of sodium and water.

Without wishing to be bound by theory, the present inventors believe that the administration of a hyperosmolar sodium load together with other electrolytes and sugar(s) and optionally trace elements at a time when the maximum effect of the iatrogenic purgative occurs reduces the gradient of change in serum osmolarity. The present inventors propose that preventing the osmolar and sodium shifts causes a reduction in the undesirable side effects seen with administration of prior art purgatives, as noted above.

DETAILED DESCRIPTION OF THE INVENTION

As used herein, the expression "minimally degradable sugar" is to be understood to mean a carbohydrate moiety that is substantially resistant to endogenous digestion in the gastrointestinal tract.

Typically, in the compositions of the invention, the minimally degradable sugar is xylose or xylotriose or mannitol. However, other sugars including oligosaccharides such as other xylooligosaccharides, fructooligosaccharides, fructosans, galactooligosaccharides and the like may be used.

Glucose and other complex sugars used in standard oral rehydration therapy lead to intestinal decomposition with the formation of gases such as methane and hydrogen which have been associated with explosion caused by diathermy (Altomare D. F. et al., *Dis Colon Rectum* 36: 291-2 (1993)). The use of minimally degradable sugars in the compositions of the present invention prevents this from occurring and reduces the incidence of abdominal cramps. In situations however where diathermy is not to be used, the minimally degradable sugar can be replaced in the compositions of the invention with a degradable sugar such as glucose, L-glucose, sucrose, fructose, galactose, or lactose.

The use of xylose (or other minimally degradable sugars) allows for transport of sodium into the alimentary cellular structure. The combination of xylose and sodium salts thus allows for replacement of electrolytes from the induced faecorrhoea, in particular sodium, potassium and chloride, and reduces the dilutional hyponatremia associated with other products such as Picoprep, Fleet and recently reported with polyethylene glycol.

Typically, in the compositions of the invention, the water-soluble sodium salt is selected from the group consisting of sodium chloride, sodium gluconate, sodium citrate and sodium aspartate.

In one form of the compositions and purgatives of the invention, they include at least one sodium salt other than sodium chloride, more preferably sodium gluconate, sodium citrate or sodium aspartate, which reduce the salty taste.

Typically, in the compositions of the invention, the water-soluble potassium salt is selected from the group consisting of potassium chloride and potassium tartrate. Usually, the ratio of potassium salt(s) to sodium salt(s) in the compositions of the invention is from about 1:1 to about 1:8, more usually from about 1:1.5 to about 1:6, still more usually from about 1:2 to about 1:5, even more usually about 1:3, on a weight basis.

Typically, in the compositions of the invention, the water-soluble magnesium salt is selected from the group consisting of magnesium sulfate, magnesium citrate and magnesium phosphate. Usually, the ratio of the weight of magnesium ions to the weight of sodium ions in the compositions of the invention is from about 1:5 to about 5:1, more usually from about 1:3 to about 3:1, still more usually from about 1:2 to about 2:1, even more usually about 1:1.

In the purgative of the second embodiment, the sodium salt or salts is/are typically present in an amount ranging from about 1-10 g, more typically about 5 g per unit dose of the purgative, which will usually be a volume of from about 0.2 to 0.5 L.

In one form, the composition of the invention comprises sodium chloride, potassium chloride, magnesium sulfate, and xylose or other minimally degradable sugars.

The composition of the invention may be used for colonscopic lavage, as a simple purgative or in electrolyte replacement therapy. The composition may be used with one or more known purgatives and in that case will complement the purgative effect of the other purgative(s) and thus reduce the amount required of these purgative agents. For example a composition of the present invention may be administered with a half dose of Fleet, or a reduced number of Picoprep capsules.

The composition may further comprise one or more further additives selected from citrate, lactate, acetate, trace elements such as calcium and zinc, nutritional elements such as Vitamin B complex, thiamine, Vitamin A, Vitamin C, Vitamin E, folic acid, and biotin. These additives may be included in the compositions of the invention in amounts which are based on the patient's daily dietary requirements.

The ratio of minimally degradable sugar(s) to sodium ions in the compositions and purgatives of the invention is from about 3:1 to 1:1 on a weight basis, and will more typically be about 2:1 to 1.4:1. The minimally degradable sugar or sugars is/are typically present in an amount ranging from about 2 to 20 g, more typically about 10 g per unit dose.

In the purgative of the second embodiment, the potassium salt or salts is/are typically present in an amount ranging from about 0.5 to 5 g per unit dose, more typically about 1 to 5 g per unit dose, still more typically about 1.5 to 3 g per unit dose.

In the purgative of the second embodiment, the magnesium salt or salts is/are typically present in an amount ranging from about 1 to about 10 g per unit dose, more typically about 3 to 5 g per unit dose.

Typically, in a purgative of the second embodiment, sodium is present at a concentration of from about 200-700 mosm. More typically, the purgative includes sodium at about three times the isotonic concentration (that is, about 270 mosm).

In the methods of the third embodiment, the composition of the invention is typically administered in an amount sufficient to provide to the patient the following quantities of the components:

(i) sodium in an amount of from about 0.01 to about 1.5 g per kg body weight, more usually about 0.05 to about 1 g per kg, still more usually about 0.08 g per kg, in which case the administered dose of sodium will approximate 5 g for an individual weighing 60-70 kg;

(ii) the minimally degradable sugar or sugars in an amount of from about 0.02 to about 3 g per kg of body weight, more usually from about 0.1 to about 0.2 g per kg, still more usually about 0.15 g per kg in which case the administered dose of minimally degradable sugar will approximate 10 g for an individual weighing 60-70 kg;

(iii) potassium in an amount of from about 0.005 to about 0.1 g per kg body weight, more usually from about 0.01 to about 0.05 g per kg, still more usually about 0.03 g per kg in which case the administered dose approximates 2 g for an individual weighing 60-70 kg;

(iv) magnesium in an amount of from about 0.01 to about 1.5 g per kg body weight, more usually about 0.05 to about 1 g per kg, still more usually about 0.08 g per kg in which case the administered dose approximates 5 g for an individual weighing 60-70 kg.

In a typical procedure, following the oral ingestion of the purgative of the invention, cool water in a volume greater than three times the volume of the purgative hypertonic solution is ingested.

The composition of the invention may further comprise a detergent stool-softening agent such as sodium picosulfate. Typically this will be present in an amount of from 5-25 mg; however more typically about 10-15 mg will be used, per unit dose of the composition.

The purgative of the second embodiment may suitably be prepared by dissolving a required amount of a composition of the first embodiment in a suitable quantity (typically from about 200 mL to 500 mL) of cold, warm or hot water.

In other forms the composition of the invention may be compressed into tablets, gel caps or capsules. In this form it is useful for pre-colonoscopic orthostatic lavage of the bowel, as preparation for barium enema, in CT "virtual colonoscopy" and for other radiological applications. It is also useful in pre-surgical lavage e.g. for removal of the bowel for cancer, diverticulitis etc. When formulated as tablets, the tablets may suitably comprise a core of the sodium, potassium and magnesium salts, surrounded by a coating of the minimally degradable sugar(s).

The composition or purgative of the invention may further comprise at least one flavouring ingredient, such as chicken, beef, vegetarian, Thai, seafood, spice or curry. Suitably, the purgative of the second embodiment is formulated as a soup or soup-like composition.

The psychological advantage of an easily tolerated fluid with versatility of flavours is that it may be substituted for a meal for patients who are on a restricted low residue clear fluids regime. Using various flavours such as chicken, beef, vegetable, kosher, gluten free, Thai, Japanese (teriyaki), Indian (curry) etc in a soup mix which includes a composition of the first embodiment allows for individual preference. If the purgative of the invention is administered as a clear soup, the purgative is typically made up using hot water rather than cool fluids. Improved tolerance and compliance is thereby achieved, in part by reducing the volume of the preparation to 350 ml and in part by providing a hypertonic "tasty" meal, as opposed to 3 liters of an unpalatable isotonic solution such as polyethylene glycol.

The purgative of the invention is an electrolyte replacement product, which may accompany and augment the action of other purgative agents such as products containing sodium picosulfate and sodium phosphate (e.g. Fleet and Picolax/Picoprep). The purgative of the invention, when administered in an effective amount to a patient, contributes to lavage but leads to fewer complications such as hyponatremia, and hypoosmolar dilutional state, and to fewer symptoms such as dizziness, nausea, headache and hypotension, than known purgative agents.

Although the ratio of individual salts in the compositions of the invention may vary within the ranges stated above, it is the combination of these salts added to a defined volume of water which forms a hypertonic salt solution. The tonicity of fluid is the key to the electrolyte replacement and purgative effect of the purgatives of the invention.

As part of the preparation involves an intact thirst mechanism which is provided by the hypertonic load, patients for whom administration of compositions of the invention is to be used with caution include the very young, the infirmed and demented, those unable to self administer water or other fluids, and those patients in which a large sodium load is undesirable (that is, patients with LVEF <25%), renal failure patients, those with advanced cardiac or renal disease and those with pituitary adenoma/hypofunction.

The invention described herein provides an electrolyte replacement lavage solution, which can have several roles. It can be administered with hyper-osmolar solutions such as products containing sodium picosulfate and sodium phosphate (e.g. Fleet and Picolax/Picoprep). It can also be used as an electrolyte replacement lavage solution for acute gastrointestinal infections including *salmonella, shigella, campylobacter* or viral gastroenteritis. This is applicable in particular to viral gastritis or bacterial gastroenteritis so as to give patient's a clearance of contents of the flora as well as replace electrolytes that are being lost during the gastroenteritis. It can also provide symptomatic improvement in those patients suffering from acute or chronic constipation and related symptoms and for those with constipation predominant irritable bowel syndrome (IBS). In addition, the product can be used alone as an effective orthostatic lavage for the following applications: prior to colonoscopy, CT scanning "virtual colonoscopy", barium enema examination, or intestinal surgery, or as a regular laxative. This is due to the product allowing simultaneous lavage of the bowel and replacement of essential electrolytes with fewer complications such as hyponatremia, hypo-osmolar dilutional state, and fewer symptoms such as dizziness, nausea and headache. The product can be used as a treatment of constipation as a regular laxative since it does not cause electrolyte losses.

The effective hypertonicity of the purgatives of the invention will cause purgation when administered to a patient undergoing a procedure for which purgation is required. These patients adhere to bowel preparation protocols which commonly instruct a low residue diet and clear fluids for 1 to 2 days prior to the procedure for which they are being prepared. In administering the purgatives of this invention a smaller volume (approximately 200-500 ml) of hyperosmolar electrolyte enhanced fluid is required as opposed to larger volumes (3-4 litres) of isotonic balanced salt solution (Glycoprep). The patients continue to consume clear fluids to maintain hydration. This is more palatable and acceptable to the patient. The volume of the purgatives of the present invention is much less (typically about one tenth) of the volume of solutions of prior art purgatives which are administered to a patient. Other fluid taken is part of a normal diet, and hence is better tolerated and more palatable, with better patient compliance.

The compositions and purgatives of the invention are particularly useful for constipation and bloating, and as soup-like preparations the purgatives of the invention are acceptable to patients as a daily food product. As a flavoured medication they have particular use as simultaneous orthostatic lavage and electrolyte replacement products in patients suffering with acute gastroenteritis. When combined with added fluids they can be used in patients with diarrhoea without dehydration. This includes traveller's diarrhoea and similar acute bacterial gut infections. The compositions and purgatives of the invention are also gluten free and therefore acceptable to those with coeliac disease.

The contained xylose and/or other minimally degradable sugar(s) (being relatively inert as opposed to glucose) in compositions of the invention is particularly important in orthostatic lavage for colonoscopy as it will help to avoid fermentation and volatile explosive gas production (e.g. methane and hydrogen). The importance of this is that the potential of an explosion during diathermy polypectomy is reduced.

One aim of the present invention is to replace lost sodium as well as water resulting from bowel preparation in intact epithelial cells devoid of toxin-induced block such as with cholera toxin Na—K ATPase pump. The use of hypertonic solutions gives an opportunity to restore the osmotic equilibrium, which is altered by the induced water intoxication following replacement of fluid without electrolytes in patients undergoing some of the established bowel preparation protocols.

In a typical method of inducing purgation of the colon in a patient, a composition of the invention is provided in the form of a sachet which includes flavouring. The contents (typically weighing about 25 g) when mixed with water, preferably heated, in a quantity of 200-500 mls (1-10 ml/kg) will form a palatable soup, which may be cool or heated to form a hypertonic preparation with an osmolarity >350 mosm/l.

After consuming the above purgative dose, the patient will be instructed to ingest cool water at least 3 times the volume, or in an adult greater than 750-1000 mls of cool water.

EXAMPLES

Formulation Examples

The following formulations illustrate the compositions of the invention. When dissolved in about 350 ml of water, they have osmolarity in the range 500-800 mosm/l. Suitably, the formulations may be mixed with about half a sachet (about 3.2 g) of commercial powdered soup mix.

Formulation 1
  Xylose 10 g
  Sodium chloride 5 g
  Potassium chloride 1.5 g
  Magnesium sulfate 5 g
  Bisacodyl 10 mg
Formulation 2
  Xylose 10 g
  Sodium chloride 5 g
  Potassium chloride 1.5 g
  Magnesium sulfate 5 g
Formulation 3
  Xylose 10 g
  Sodium chloride 5 g
  Potassium chloride 1.5 g
  Magnesium sulfate 5 g
  Sodium picosulfate 10 mg
Formulation 4
  Sodium chloride 10 g
  Xylose 14 g
  Potassium chloride 3 g
  Magnesium sulfate 3 g
Formulation 5
  Xylose 10 g
  Sodium citrate 3 g
  Sodium chloride 2 g
  Potassium chloride 2 g
  Magnesium sulfate 5 g
  Sodium picosulfate 15 mg
Formulation 6
  Xylose 8 g
  Sodium chloride 3 g
  Sodium citrate 2 g
  Potassium chloride 2 g
  Magnesium sulfate 10 g
  Sodium picosulfate 15 mg

EXAMPLES OF ADMINISTRATION OF COMPOSITIONS OF THE INVENTION

Administration Example 1

At time zero 3 Bisacodyl 5 mg tabs and 350 ml of soup containing Formulation 1 and 3.2 g of a commercial powdered soup mix were taken by a normal male subject (75 kg) in two doses spaced ½-1 hour apart. Alternatively, the Formulation 1 may be added to the Bisacodyl preparation in the form of a capsule.

At the time of taking the preparation, side effects experienced were irritability and indigestion. Two large cups of water were drunk freely by the patient before and after administration of the formulation. At 1.5 hour commenced watery diarrhoea with minimal gas, which continued about every 10 minutes for 1 hour (i.e. 6 occasions) with decreasing amounts of faecal matter. At 3-4 hours no adverse affects were observed.

Administration Example 2

350 ml of soup containing Formulation 2 and 3.2 g of a commercial powdered soup mix were taken by a normal male subject (75 kg) over 15 minutes followed by 1 litre of cold water. At 1½ hours watery evacuation commenced with no flatulence and continued at intervals of 10 minutes for 45 minutes then ceased. No cramps and no headaches are associated with the treatment.

Administration Example 3

Formulations 5 and 6, which include sodium citrate and have improved palatability, were administered as 350 ml of warm soup containing 3.2 g of a commercial powdered soup mix, with similar results as above. That is, 5 loose watery motions occurred over 1-1½ hours duration after administration.

Administration Example 4

Combination with Picosulfate in Patient Undergoing Colonoscopy

Formulation 3 above was used in a 40-year-old woman with previously good health. Two sachets, each containing formulation 3 and 3.2 g of commercial powdered soup mix (one chicken flavoured and one beef flavoured) were given six hours apart and cleaned the bowel to enable colonoscopic evaluation without any complaints from the patient of side effects of headache or lightheadedness.

Administration Example 5

Combination with Picoprep Capsules

A 72 year old male with a history of right hemicolectomy for carcinoma of colon and constipation was given a single sachet containing formulation 5 and 3.2 g of commercial powdered soup mix in 350 ml water at 3 pm. This was followed by nine watery motions, which commenced fifteen minutes after drinking the soup. The instruction was to drink one litre of water following the soup. The patient then took five one gram capsules of "Picoprep" at 6 pm, again accompanied with one litre of water and had six further loose motions. Overnight he had three loose motions. A colonoscopy was successfully performed the next day at 11 am. There were no reported side effects.

Administration Example 6

Treatment of Gastroenteritis

A child of 8 years with symptoms of crampy abdominal pain was given a third of the amount of formulation 2 with onset of loose motions within 1-2 hours and resolution of symptoms and no untoward effect.

Administration Example 7

Treatment of Constipation

A 48 year lady with long standing constipation was given a single preparation of formulation 3 as a soup containing 3.2 g of commercial powdered soup mix and developed a result after one to one and a half hours of taking the formulation. There were four episodes in the space of ninety minutes when she had to evacuate her bowel and apart from complaining of the "saltiness" of the preparation it was well tolerated.

Administration Example 8

A 67 year old lady with a family history of colonic carcinoma and single polyp removed three years prior was returning for her surveillance colonoscopy. At the previous colonoscopy she had used picosulfate—two sachets which resulted in profound hyponatremia associated with nausea and vomiting, malaise and severe headache. She required intravenous fluids prior to colonoscopy. On return for surveillance colonscopy three years later the patient was afraid to take the picosulfate because she was concerned about developing the same complications. As a result she was given the two sachets of picosulfate but this time also with two sachets of Formulation 3 mixed in beef flavoured soup. These were given six hours apart. The bowel was cleansed to the caecum with excellent mucosal views. This time the patient did not develop any nausea, vomiting, headaches, light headedness or malaise. Her serum electrolytes were normal when tested.

INDUSTRIAL APPLICABILITY

The compositions of this invention are useful for colonoscopic lavage, as simple purgatives or in electrolyte replacement therapy, as preparations for barium enema, in CT "virtual colonoscopy" and for other radiological applications, as electrolyte replacement lavage solutions for acute gastrointestinal infections, for symptomatic improvement in those patients suffering from either acute or chronic constipation and related symptoms, or as a regular laxative.

The invention claimed is:
1. A purgative composition, comprising
 (i) 1-10 gram per unit dose of at least one water-soluble sodium salt;
 (ii) 2-20 gram per unit dose of at least one water-soluble minimally degradable sugar;
 (iii) 0.5 to 5 gram per unit dose of at least one water-soluble potassium salt;
 (iv) 1-10 gram per unit dose of at least one water-soluble magnesium salt; and
 (v) a detergent stool softening agent, selected from the group consisting of sodium picosulfate and bisacodyl;
 wherein the composition is a hypertonic composition in the form of a unit dose having a volume of from about 0.2 to 0.5 L; and wherein the minimally degradable sugar is selected from the group consisting of xylose and xylotriose.
2. The purgative composition of claim 1, wherein the water-soluble sodium salt is selected from the group consisting of sodium chloride, sodium gluconate, sodium citrate, sodium aspartate and mixtures thereof.
3. The purgative composition of claim 1, wherein the water-soluble potassium salt is selected from the group consisting of potassium chloride and potassium tartrate.
4. The purgative composition of claim 1, wherein the water-soluble magnesium salt is selected from the group consisting of magnesium sulfate, magnesium citrate and magnesium phosphate.
5. The purgative composition of claim 1 further comprising at least one composition or additive selected from the group consisting of a flavouring ingredient, a detergent stool-softening agent, citrate, lactate, acetate, a trace element and a nutritional element.

6. The purgative composition of claim 1 in the form of, or formulated as, a soup or soup-like composition, tablet, gel cap, capsule or sachet.

7. A method of inducing purgation of the colon of a patient in need thereof, comprising administering to the patient a purgative composition of claim 1 in an amount effective to induce purgation of the patient's colon.

8. The composition of claim 1, wherein the minimally degradable sugar comprises a xylose.

9. The purgative composition of claim 1, wherein:
(i) the at least one water-soluble sodium salt comprises sodium chloride;
(ii) the at least one water-soluble minimally degradable sugar comprises a xylose;
(iii) the at least one water-soluble potassium salt comprises a potassium chloride; or
(iv) the at least one water-soluble magnesium salt comprises magnesium sulfate.

10. The purgative composition of claim 1, further comprising one or more compositions or additives selected from the group consisting of a citrate, a lactate, an acetate, a calcium, a zinc, a Vitamin B complex, a thiamine, a Vitamin A, a Vitamin C, a Vitamin E, a folic acid and a biotin.

11. The purgative composition of claim 1, wherein the detergent stool softening agent is sodium picosulfate.

12. The purgative composition of claim 1, wherein the detergent stool softening agent is bisacodyl.

13. The purgative composition of claim 1 in the form of:
(a) a tablet, or
(b) a tablet comprising:
  a core comprising the sodium, potassium and magnesium salts; and
  a coating comprising the minimally degradable sugar(s); wherein the coating surrounds the core.

14. The method of claim 7, wherein:
the at least one water-soluble sodium salt comprises a sodium chloride, a sodium gluconate, a sodium citrate or a sodium aspartate;
the at least one water-soluble potassium salt comprises a potassium chloride; or
the at least one water-soluble magnesium salt comprises a magnesium sulfate, a magnesium citrate or a magnesium phosphate.

15. The purgative composition of claim 1 in the form of, or formulated as, a medicament.

* * * * *